United States Patent [19]

Blanke

[11] 4,230,554
[45] Oct. 28, 1980

[54] APPARATUS FOR MEASURING IONS IN SOLUTION

[75] Inventor: Gordon C. Blanke, Brea, Calif.

[73] Assignee: Beckman Instruments, Inc., Fullerton, Calif.

[21] Appl. No.: 921,401

[22] Filed: Jul. 3, 1978

[51] Int. Cl.³ .............................................. G01N 27/44
[52] U.S. Cl. .................................. 204/195 T; 324/425
[58] Field of Search .............. 204/1 M, 195 T, 195 R; 324/29, 425

[56] References Cited

U.S. PATENT DOCUMENTS

| | | | |
|---|---|---|---|
| 3,242,729 | 3/1966 | Keller | 204/195 R X |
| 3,486,998 | 12/1969 | Sellers et al. | 204/195 T |
| 3,776,832 | 12/1973 | Oswin et al. | 204/195 R |
| 3,788,962 | 1/1974 | Frenck | 204/195 C |
| 3,881,997 | 5/1975 | Johnson et al. | 204/1 T |
| 4,007,105 | 2/1977 | Buzza et al. | 204/195 T |
| 4,048,041 | 9/1977 | David et al. | 204/195 R |
| 4,066,528 | 1/1978 | Mansfield | 204/195 T |
| 4,118,300 | 10/1978 | Victor et al. | 204/195 T |

FOREIGN PATENT DOCUMENTS 2627487 12/1977 Fed. Rep. of Germany ...... 204/195 R

Primary Examiner—G. L. Kaplan
Attorney, Agent, or Firm—Robert J. Steinmeyer; Robert R. Meads; John R. Shewmaker

[57] ABSTRACT

Titration apparatus for measuring chloride electrolyte in blood samples including a pair of coulometric generating electrodes (anode and cathode) for titrating the chloride with silver ions to precipitate silver chloride and a pair of amperometric detecting electrodes for detecting uncombined silver ions following complete titration of the chloride and hence for signaling the endpoint of the chloride titration. A predetermined potential difference is applied across the amperometric electrodes, and an operating condition of zero current flow is established through one of the amperometric electrodes. Current flow between the amperometric electrode and the coulometric anode is monitored to indicate the presence of uncombined silver ions and thereby the titration endpoint.

5 Claims, 1 Drawing Figure

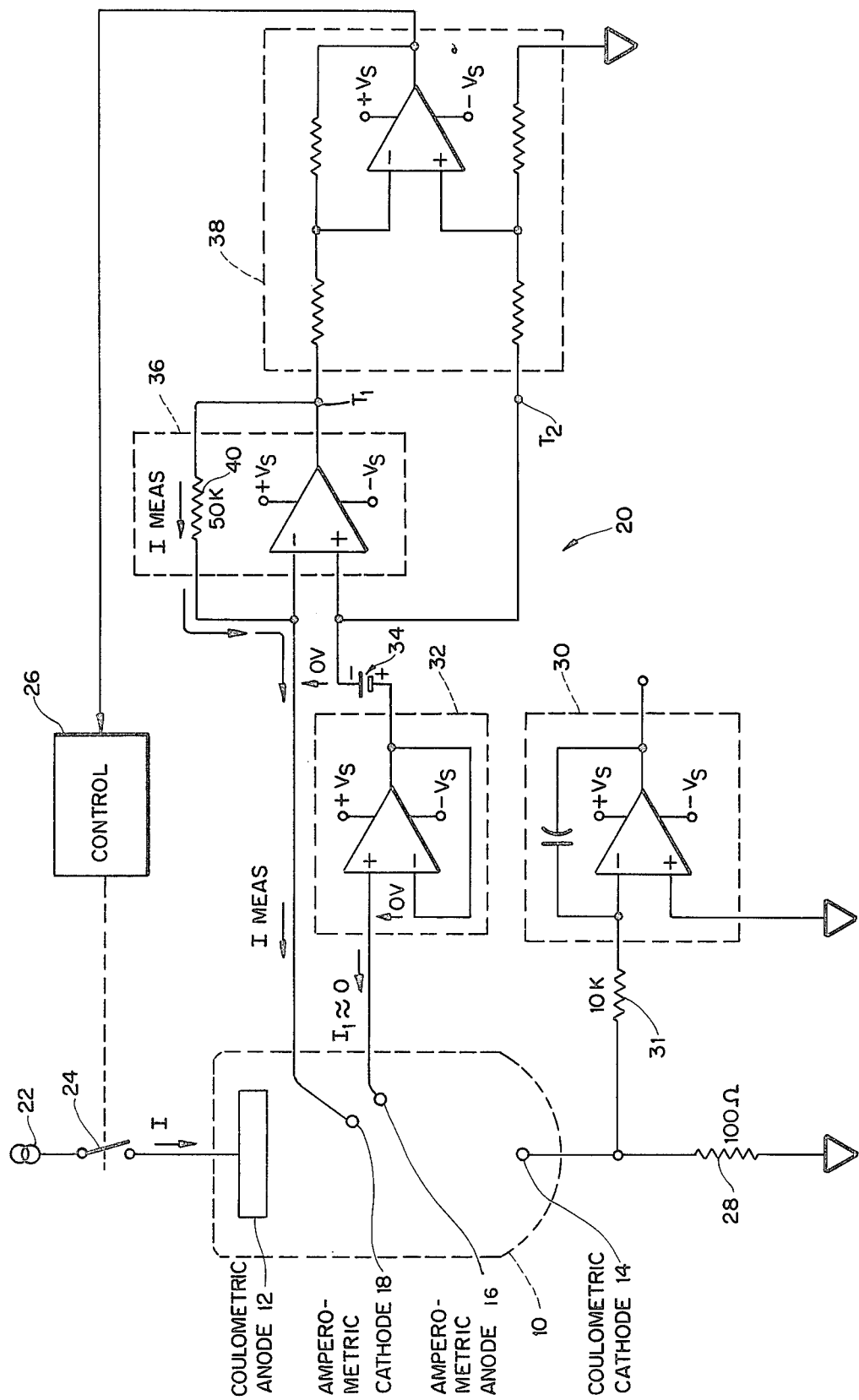

APPARATUS FOR MEASURING IONS IN SOLUTION

BACKGROUND OF THE INVENTION

1. Field of the Invention

The present invention relates generally to the detection of ions in solution and, more particularly, to apparatus for monitoring an ionic species to determine the progress of an electrochemical titration operation.

2. Description of the Prior Art

Electrochemical titrators have long been available for analyzing chemical, biological, or biochemical substances such as blood serum. U.S. Pat. No. 4,007,105, assigned to the assignee of the present invention, describes a titrator adapted for analyzing chloride electrolyte in blood samples by coulometrically generating silver ions which combine with and precipitate the chloride as silver chloride and by amperometrically detecting the endpoint of the titration by detecting the presence of excess, uncombined silver ions. Upon detecting such uncombined ions, the coulometric generator is disabled. By measuring the coulometric current flow during a titration, and hence measuring the quantity of silver ions generated in order to precipitate the chloride, a quantitative measure of the chloride level in the blood sample is obtained.

The foregoing titrator employs a coulometric generator comprising a large silver coulometric anode and a smaller platinum cathode, and an amperometric detector comprising a pair of small silver electrodes. During titration silver ions are liberated from the coulometric anode which disintegrates over a period of time. With this in mind, the coulometric anode is made relatively large to increase its operating life and is designed to be readily replaced with a new electrode as required.

The small silver amperometric electrode pair operate to detect the presence of uncombined silver ions following precipitation of all of the sample chloride. To this end, a relatively small predetermined potential difference (e.g., 100 mv) is applied across the amperometric electrodes. During titration, the silver ions liberated from the coulometric anode combine with the sample chloride. At such time no excess uncombined silver ions are present and hence no significant current flow takes place between the amperometric electrodes. When all chloride is precipitated, further generation of silver ions by the coulometric generator introduces excess silver ions into the solution. Such excess uncombined ions enable a substantially larger current to flow between the amperometric detecting electrodes and this current flow is employed to signal the end of the titration and to initiate a turn-off of the coulometric generator.

A drawback of the foregoing amperometric detecting arrangement resides in the fact that the flow of current therebetween liberates silver ions from the amperometric anode and hence the amperometric anode slowly disintegrates by such action. Since the amperometric anode is by design relatively small, any disintegration should be minimized. This is particularly critical where all electrodes (except the large coulometric anode) are combined in a single electrode module, as taught in the foregoing patent. Obviously, the useful life of the module is limited to that of the shortest lived electrode—herein the amperometric anode.

SUMMARY OF THE INVENTION

Briefly, and in general terms, the present invention resides in an electrochemical titration apparatus which overcomes the disadvantages of the prior arrangements. To this end, the amperometric detecting electrode pair is operated by applying a predetermined potential difference therebetween while establishing an operating condition at one amperometric electrode of substantially zero current flow therethrough. Uncombined ions present at the end of a titration establish a current flow between the other amperometric electrode (cathode) and the coulometric anode, and this current is employed to signal the end of a titration and to inhibit the coulometric generator. In the foregoing manner, neither amperometric electrode is consumed in detecting the titration endpoint, but instead the current flow between the amperometric cathode and the coulometric anode causes further disintegration of the coulometric anode which is a consumable electrode by design.

In the preferred embodiment of the invention, a first one of the amperometric electrodes is connected to one input terminal of a high impedance voltage follower amplifier, the output terminal of which is directly connected back to the other input terminal thereof. The second amperometric electrode is connected to one input terminal of a current-to-voltage converter, and the output terminal of the voltage follower amplifier is coupled through a predetermined potential source to the other input terminal of the converter. With this arrangement, current flow through the first amperometric electrode is prevented by the high impedance connection to the follower amplifier, and the predetermined voltage generated by the potential source is connected across the pair of amperometric electrodes. The resulting current flow between the second amperometric electrode and the coulometric anode indicates the level of excess ions present. This current is converted to a control voltage by the current-to-voltage converter and the control voltage is employed to signal the titration endpoint and inhibit the coulometric generator.

BRIEF DESCRIPTION OF THE DRAWING

The sole FIGURE of the drawing illustrates in schematic form a preferred form of the electrochemical titration apparatus of the invention.

DESCRIPTION OF THE PREFERRED EMBODIMENT

As shown in the drawing for purposes of illustration, the present invention is embodied in titration apparatus including an analysis cell 10 comprising a coulometric generating electrode pair 12 and 14, an amperometric detecting electrode pair 16 and 18, and a novel amperometric detecting circuit arrangement, indicated generally by numeral 20, for monitoring operation of the titration apparatus and signalling the end point of a titration operation. A preferred structure of analysis cell 10 and the four operative electrodes therein is that depicted in aforementioned U.S. Pat. No. 4,007,105. The coulometric electrodes form part of a coulometric generator for introducing silver ions into the cell while the amperometric electrodes form part of an amperometric detector for monitoring the level of uncombined silver ions to signal complete titration of the sample. For the generation and detection of silver ions, coulometric anode 14 and both amperometric electrodes 16 and 18 are silver, while coulometric cathode 14 is platinum. As indicated previously, during titration silver ions are liberated from coulometric anode 12, and for this reason the anode is relatively large and is designed to be readily replaced when consumed. The remaining three electrodes are incorporated in a single replaceable electrode module. The foregoing patent is specifically incorporated herein by reference for further details regarding the structure of cell 10 and electrodes 12-18.

Coulometric anode 12 is connected to a current source 22 by a switch 24 when switch 24 is closed in response to action of a control 26. Coulometric cathode 14 is connected to circuit ground through a current-dividing resistor pair 28 and 31, and the fraction of current through resistor 31 is fed to a conventional integrater 30. With switch 24 closed, a coulometric current flow is established between coulometric electrodes 12 and 14 causing silver ions to be liberated from coulometric anode 12. Integrator 30 integrates the predetermined fraction of the resulting current flow through resistor 31 to derive a measure of the silver ions thus generated.

As taught in the referred patent, the titration apparatus is operated by filling the analysis cell 10 with dilute sulfuric acid reagent and initially titrating any chloride in the reagent to establish an equilibrium or base line silver ion concentration value before adding a blood sample to the reagent. To this end, switch 24 is closed to enable the coulometric generator and a predetermined voltage (100 mv) is applied across amperometric detecting electrodes 16 and 18. When the reagent chloride has precipitated as silver chloride, the silver ions thereafter generated remain as excess, uncombined ions. The excess ions result in an increased current flow in the amperometric detecting circuit 20. When an amperometric current level indicative of the desired equilibrium silver ion concentration is reached, control 26 opens switch 24 to disable the coulometric generator. Subsequently, a blood sample is injected into the reagent and stirred in a conventional manner. The excess silver ions present in the reagent combine with sample chloride to precipitate silver chloride. The resulting decrease in the equilibrium silver ion level is sensed by the amperometric detecting circuit 20 which closes switch 24 through control 26 to enable the coulometric generator to liberate silver ions from the coulometric anode 12. A coulometric current flow is thus again established between coulometric electrodes 12 and 14. As long as sample chloride is present, the liberated silver ions combine therewith to precipitate silver chloride. Upon complete titration of the sample chloride, further ions liberated from coulometric anode 12 remain as excess ions in solution and enable current to flow in the amperometric detecting circuit 20. When the uncombined silver ion concentration reaches the former base line or equilibrium level, the amperometric detecting circuit again opens switch 24 through control 26 to disable the coulometric generator. Integrator 30 connected to coulometric cathode 14 integrates the coulometric current flow to provide a measure of the quantity of ions generated and hence of the sample chloride concentration.

In the foregoing respects the operation of the coulometric generator arrangement is conventional and corresponds to the operation of the coulometric generator employed in the titrator of the aforementioned patent.

Amperometric detection circuitry 20, as connected across amperometric electrodes 16 and 18, includes a high input impedance voltage follower amplifier 32, a source of predetermined potential 34, a current-to-voltage converter 36, and a difference amplifier 38. Follower amplifier 32, converter 36, and amplifier 38 (as well as integrator 30) all employ conventional operational amplifiers having inverting and non-inverting input terminals, an output terminal, and a pair of supply voltage terminals having a supply potential $\pm V_S$ connected thereacross. The operational amplifiers are high gain devices, preferably exhibiting a gain of at least 10,000 or more. The output terminal of amplifier 32 is directly connected back to the inverting input terminal thereof. The output terminal of converter 36 is connected through a current measuring resistance 40 to the non-inverting input terminal thereof.

The potential source 34 supplies a predetermined potential to be applied across electrodes 16 and 18. In the illustrated embodiment source 34 provides a 100 mv output. Such may be conveniently derived, for example, by a voltage divider resistor pair connected across a 1.5 v battery, the resistor values being selected to divide the battery voltage coupled thereacross to supply a 100 mv output potential across one resistor of the pair.

In accordance with a primary aspect of the present invention the amperometric anode 16 is connected to one input terminal of the voltage follower amplifier 32 and the amperometric cathode 18 is connected to one input terminal of current-to-voltage converter 36. The output terminal of the follower amplifier 32 is connected through predetermined potential source 34 to the non-inverting input terminal of the converter 36. Thus arranged, follower amplifier 32 drives the potential difference between its input terminals toward substantially zero volts so that the output potential of the amplifier follows the potential of the amperometric anode 16 with substantially no potential drop across the amplifier. Significantly, in view of the high input impedance of amplifier 32, preferably $10^8$ ohms or more, substantially no current ($I_1$) is drawn through its non-inverting input terminal and hence no current flows through amperometric anode 16 (i.e. $I_1 \cong 0$).

Current-to-voltage converter 36 likewise drives the potential difference at its input terminals toward substantially zero volts. Consequently, the amperometric detecting circuitry 20 effectively applies the predetermined potential of the source 34 (e.g. 100 mv) across amperometric electrodes 16 and 18. This is apparent by summing voltages around a loop connecting the amperometric electrodes. For example, beginning at amperometric anode 16 the potentials include (1) substantially zero volts across follower amplifier 32, (2) the predetermined voltage of source 34, and (3) substantially zero volts across the input terminals of current amplifier 36. With the predetermined potential thus applied across amperometric electrode 16 and 18, an amperometric current would normally flow there between having a value related to the excess ion concentration in the solution.

It has been discovered that with current $I_1$ through amperometric anode 16 constrained to substantially zero, a current $I_{MEAS}$ flows through amperometric cathode 18 and current measuring resistor 40 of current-to-voltage converter 36. Moreover, the value of $I_{MEAS}$ has been found to correlate with the silver ion concentration value in analysis cell 10. Since current flow through amperometric anode 16 is precluded, a path for the flow of $I_{MEAS}$ includes the coulometric generator and presummably coulometric anode 12 thereof. Beyond this, with substantially zero current through amperometric anode 16, it does not disintegrate by the liberation of silver ions. Instead, $I_{MEAS}$ is supported by the liberation of silver ions from coulometric anode 12.

The value of $I_{MEAS}$ through current measuring resistance 40 is monitored by conventional difference amplifier 38 and converted to an output control voltage signal coupled to control 26. Difference amplifier includes first and second input terminals $T_1$ and $T_2$ connected, respectively, to one terminal of resistor 40 and to the non-inverting input of converter 36. With one terminal of resistor 40 thus connected to $T_1$, the second resistor terminal (connected to inverting input of converter 36) is effectively connected to $T_2$ since converter 36 drives the potential difference between its input terminals to a value approaching zero volts. Since difference amplifier is referenced to circuit ground, it rejects the common mode voltage at its inputs and effectively supplies at its output an output control relative to ground which is proportional to current $I_{MEAS}$ through resistor 40 and amperometric cathode 18 and hence proportional to the silver ion concentration in analysis cell 10. As a result, the value of this control voltage may be employed to signal the titration endpoint upon detecting the predetermined equilibrium silver ion concentration level. At such time, the output of amplifier 38 enables control 26 to open switch 24 to disable the coulometric generator.

In operation of the titrator, sulphuric acid reagent is introduced into the analysis cell 10, and the coulometric generator is enabled by control 26 closing switch 24 to precipitate any chloride in the reagent. After precipitating all reagent chloride, excess silver ions are introduced into the cell, and the excess ions are available to enable a current path between amperometric electrodes 16 and 18. However, because amperometric anode is constrained to operate at substantially zero current therethrough, current $I_{MEAS}$ flows between amperometric cathode 18 and coulometric anode 12 with a value related to the excess ion concentration. When the output voltage from amplifier 38 indicates an $I_{MEAS}$ value corresponding to a equilibrium or base line silver ion concentration level, control 26 responsive thereto disables the coulometric generator by opening switch 24. Thereafter, a blood sample is introduced into the reagent, and the coulometric generator is enabled to precipitate the sample chloride. The coulometric generator is enabled until all sample chloride is precipitated and the equilibrium silver ion concentration value is restored in the analysis cell. Integrator 30 integrates the coulometric current for the titration and provides the measure of the chloride. As the equilibrium silver ion concentration value is approached, $I_{MEAS}$ increases until attaining a value necessary to disable the coulometric generator in the previously described manner. In the foregoing process, the current flow between coulometric anode 12 and amperometric cathode 18 liberates silver ions from the coulometric anode but not from the amperometric electrode. As a result, amperometric anode is not consumed and its useful life is thereby extended. While the life of coulometric anode 12 will be shortened somewhat, such poses little problem since anode 12 is intentionally designed as a relatively large, consumable and replaceable electrode.

While detecting circuitry 20 of the invention has been illustrated and described for the detection of silver ions in an electrochemical titration apparatus, it will be understood that the circuitry may be employed for measuring concentration of ions is solution in applications other than titrators. In such applications, with current $I_1$ again substantially zero through electrode 16, a third electrode is provided contacting the solution for completing a path for current flow $I_{MEAS}$ through electrode 18 and the third electrode in the manner which the coulometric electrode completed the current path in the illustrated embodiment.

While a preferred embodiment of the invention has been illustrated and described, it will be apparent that modifications may be made therein without departing from the spirit and scope of the invention as defined by the appended claims.

What is claimed is:

1. Electrochemical titration apparatus for measuring a constituent of a sample in solution and including coulometric generating means for generating ions combinable with the sample constituent and amperometric detecting means for detecting the presence of uncombined ions in said solution, each of said coulometric generating means and said amperometric detecting means including a respective pair of electrodes for contacting said sample in solution, the improvement comprising:

means for enabling said coulometric generating means;

means for applying a predetermined potential difference between the amperometric detecting electrodes while simultaneously establishing an operating condition of substantially zero current flow at one of said amperometric detecting electrodes; and means for monitoring flow of current between the other of said amperometric detecting electrodes and one of said coulometric generating electrodes.

2. The apparatus of claim 1 further including:

means for disabling said coulometric generating means in response to a predetermined value of said flow of current.

3. The apparatus of claim 1 wherein said means for applying a predetermined potential difference includes:

high input impedance voltage follower means;

a potential source;

the voltage follower means having a high impedance input terminal connected to said one amperometric detecting electrode and having an output terminal connected to a first terminal of said potential source; and means for connecting a second terminal of said potential source to said other amperometric detecting electrode.

4. The apparatus of claim 3 wherein said means for connecting includes current-to-voltage converter means having one input terminal connected to said second terminal of said potential source and a second input terminal connected to said other amperometric detecting electrode, and resistance means connected between an output terminal and said second input terminal of said converter means whereby said flow of current is through said resistance means.

5. The apparatus of claim 4 further including difference amplifier means having first and second inputs effectively connected across said resistance means and having an output terminal supplying a control voltage signal proportional to said flow of current.

* * * * *